United States Patent [19]
Stein

[11] Patent Number: 4,794,192
[45] Date of Patent: Dec. 27, 1988

[54] CYCLIC AMINOALKYLSILANES AND THEIR USE AS ADHESION PROMOTERS IN ROOM TEMPERATURE VULCANIZABLE POLYDIORGANOSILOXANE COMPOSITIONS

[75] Inventor: Judith Stein, Schenectady, N.Y.

[73] Assignee: General Electric Company, Schenectady, N.Y.

[21] Appl. No.: 70,009

[22] Filed: Jul. 6, 1987

[51] Int. Cl.[4] ........ C07F 7/10
[52] U.S. Cl. ........ 556/408
[58] Field of Search ........ 556/408

[56] References Cited

U.S. PATENT DOCUMENTS

| | | | |
|---|---|---|---|
| 2,946,701 | 7/1960 | Plueddemann | 117/72 |
| 3,220,878 | 11/1965 | Pines | 556/408 X |
| 3,334,121 | 8/1967 | Pepe et al. | 260/448.2 |
| 3,387,016 | 6/1968 | Nitzsche et al. | 260/448.8 |
| 3,448,137 | 6/1969 | Niederprüm et al. | 556/408 |
| 3,620,984 | 11/1971 | Dahm et al. | 556/408 X |
| 3,723,492 | 3/1973 | Möller et al. | 556/408 |

FOREIGN PATENT DOCUMENTS

| | | | |
|---|---|---|---|
| 2273548 | 2/1976 | France | 556/408 |

*Primary Examiner*—Paul F. Shaver
*Attorney, Agent, or Firm*—William H. Pittman; James C. Davis, Jr.; James Magee, Jr.

[57] ABSTRACT

Cyclic aminoalkylsilane compositions are prepared by the reaction of approximately equimolar amounts of an aminoalkyltrialkoxysilane such as 3-aminopropyltrimethoxysilane and a glycidyl ether such as methyl glycidyl ether. They are useful as adhesion promoters in room temperature vulcanizable compositions comprising polyalkoxysilyl-terminated polydiorganosiloxanes.

4 Claims, No Drawings

CYCLIC AMINOALKYLSILANES AND THEIR USE AS ADHESION PROMOTERS IN ROOM TEMPERATURE VULCANIZABLE POLYDIORGANOSILOXANE COMPOSITIONS

This invention relates to new compositions of matter, and more particularly to cyclic silicon-nitrogen compounds useful as adhesion promoters in room temperature vulcanizable compositions.

Considerable attention has been directed in recent years to the development of improved one-package room temperature vulcanizable (hereinafter sometimes designated "RTV") compositions. Under ideal conditions, these compositions would be stable for an indefinite period when stored in the absence of moisture, and would promptly cure to a tack-free elastomer upon contact with moisture, including the relatively small proportions of water vapor present in the atmosphere.

In a typical RTV composition, the predominant constituent is a polydiorganosiloxane (hereinafter sometimes designated "silicone" for brevity) containing polyalkoxysilyl end groups, typically dialkoxyalkylsilyl groups. Said end groups are capable of being cross-linked by atmospheric moisture in the presence of a suitable metal-containing catalyst, usually an aluminum, titanium or tin compound. Disclosures of RTV compositions of this type are present in many patents and publications.

A particularly useful one-package RTV composition is disclosed in U.S. Pat. No. 4,517,337. It employs a catalyst such as dibutyltin bis(acetylacetonate), which is stable in the presence of hydroxy species such as methanol and silanol-terminated silicones and may therefore be employed without scavengers for such hydroxy species.

Many RTV compositions have inadequate adhesion to various substrates, particularly metals such as aluminum and steel. Therefore, it is a common practice to employ adhesion promoters, typically various silicon-nitrogen compounds, in such compositions.

The present invention provides a class of novel silicon-nitrogen compounds useful as adhesion promoters, and a method for their preparation. It also provides novel RTV compositions containing said adhesion promoters, particularly scavenger-free compositions containing tin complex catalysts such as dialkyltin bis(acetylacetonates).

In one of its aspects, the present invention includes compositions comprising cyclic aminoalkylsilanes having the formula

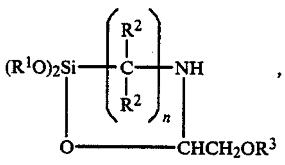 ,  (I)

wherein $R^1$ is $C_{1-8}$ alkyl, each $R^2$ is independently hydrogen or $C_{1-4}$ primary or secondary alkyl, $R^3$ is methyl or ethyl and n is 2 or 3.

The $R^1$ radicals in the cyclic aminoalkylsilanes of this invention are $C_{1-8}$ alkyl radicals, usually methyl. The $R^2$ radicals may be hydrogen or alkyl radicals as indicated and are usually hydrogen, and $R^3$ is methyl or ethyl and usually methyl. The value of n is 2 or 3, usually 3.

The cyclic aminoalkylsilane compositions of this invention may be prepared by effecting reaction at a temperature in the range of about 60°-125° C. between approximately equimolar amounts of an aminoalkyltrialkoxysilane of the formula

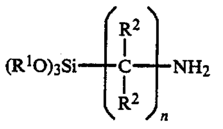  (II)

and a glycidyl ether of the formula

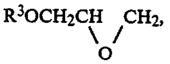  (III)

wherein $R^{1-3}$ and n are as previously defined. This method of preparing silicon-nitrogen compositions is another aspect of the invention.

Most often, this reaction may be conveniently conducted by heating a mixture of the two reagents under reflux, ordinarily in an inert atmosphere such as nitrogen. As previously stated, approximately equimolar proportions of the two are employed; if an excess of either is present, it should typically be no more than about 5%. While solvents may be employed, they generally offer no particular advantage and therefore are not preferred.

As previously indicated, the cyclic aminoalkylsilane compositions of this invention are useful as adhesion promoters in RTV compositions. Accordingly, another aspect of the invention is a method for improving adhesion to a substrate of such a composition comprising a polyalkoxy-terminated polydiorganosiloxane (silicone) and a catalytic amount of a curing catalyst, said method comprising incorporating therein an effective amount, typically about 0.1-5.0 parts per 100 parts of said polyalkoxysilyl-terminated polydiorganosiloxane, of said cyclic aminoalkylsilane composition.

Still another aspect of the invention is RTV compositions comprising (A) at least one polyalkoxy-terminated silicone, (B) a catalytic amount of a curing catalyst, and (C) an amount effective to enhance adhesion to a substrate of said cyclic aminoalkylsilane.

The polyalkoxysilyl-terminated silicones useful as component A may be represented by the formula

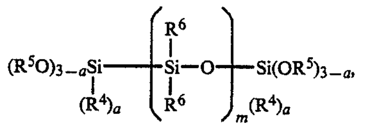  (IV)

wherein $R^4$ is an unsubstituted or substituted hydrocarbon radical containing from 1 to about 13 carbon atoms, $R^5$ is an alkyl, alkoxyalkyl, acylalkyl, acyloxyalkyl or cyanoalkyl radical containing from 1 to about 8 carbon atoms or an aralkyl radical containing from 1 to about 14 carbon atoms, each $R^6$ is independently an unsubstituted or substituted hydrocarbon radical containing about 1-13 carbon atoms, a is 0 or 1 and m is in the range of about 5-5000. Illustrative $R^4$ and $R^6$ radicals are methyl, ethyl, phenyl, trifluoropropyl and vinyl.

Alkyl radicals having up to about 4 carbon atoms and especially methyl radicals are preferred. $R^5$ may be alkyl or the designated substituted alkyl radicals containing aryl, ethyl, ester, ketone or cyano substituents; it is also most often $C_{1-4}$ alkyl and especially methyl. The value of a is 0 or 1 and most often 1.

Component A may be prepared in situ in the RTV composition by the reaction of a silanol-terminated silicone and, as an endcapping reagent, a polyalkoxysilane such as methyltrimethoxysilane, in accordance with U.S. Pat. No. 4,395,526. It may also be previously formed by the same reaction, most often in the presence of a catalyst as disclosed, for example, in U.S. Pat. No. 4,515,932 and copending, commonly owned application Ser. No. 225,992. The time of its formation is not critical for the purposes of this invention, although it is frequently preferred to employ a previously formed polyalkoxylsilyl-terminated silicone.

Component B, the curing catalyst, may be any of the metal-containing catalysts known in the art. As previously noted, these are usually aluminum, titanium or tin compounds. In a particularly preferred embodiment of the invention, the catalyst is an organotin complex of the formula

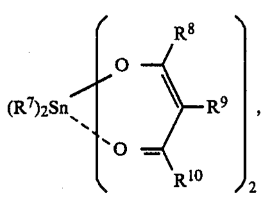
(V)

wherein $R^7$ is an unsubstituted or substituted hydrocarbon radical containing from 1 to about 18 carbon atoms and each of $R^8$, $R^9$ and $R^{10}$ is independently hydrogen, $R^7$, $Si(R^7)_3$, acyl or nitrile.

Component C, the cyclic aminoalkylsilane composition of the present invention, is employed in the RTV composition as an adhesion promoter. Its action as such is frequently optimized if it is employed in combination with (D) a cyanoalkyltrialkoxysilane, most often 2-cyanoethyltrimethoxysilane (hereinafter "CETMS") or 3-cyanopropyltrimethoxysilane, which acts as a synergist therefor.

Components B and C are present in the RTV compositions of this invention in effective proportions to serve as catalysts and adhesion promoters, respectively. In general, about 0.1-10.0 parts of component B and about 0.1-5.0 parts of component C are employed per 100 parts of component A. When employed, component D is usually present in the amount of about 0.1-5.0 parts per 100 parts of component A.

The RTV compositions of the invention may also contain other constituents in common use in such compositions, including curing catalyst accelerators, scavengers for hydroxy species, plasticizers, pigments and fillers. In particular, at least one of the following may be present, all proportions being per 100 parts of component A:

(E) about 0.05-5.0 parts of a diketone of the formula

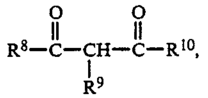
(VI)

wherein $R^{8-10}$ are as previously defined;

(F) about 0.01-10.0 parts of at least one polyalkoxysilane of the formula $$(R^4)_aSi(OR^5)_{4-a} \quad \text{(VII)}$$

wherein $R^{4-5}$ and a are as previously defined;

(G) about 1-50 parts of a plasticizer;

(H) about 5-700 parts of at least one filler; and (J) about 0.1-5.0 parts of an amine or guanidine as a curing accelerator.

Components E and F are often particularly preferred other constituents. Their presence contributes to the shelf stability of the RTV compositoon in the absence of moisture and its rapidity of cure in the presence of moisture.

The presence of component G is also frequently preferred. Suitable plasticizers useful as component G include trialkylsilyl-terminated polydiorganosiloxanes of the formula

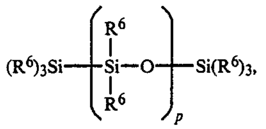
(VIII)

wherein $R^6$ is as previously defined and p is in the range of about 25-5000.

The presence or absence of component H, the filler, will depend to some extent on the intended use of the RTV composition. When the composition is to be used as a construction sealant or caulking compound, relatively large proportions of filler may be employed. For other uses, minor proportions of filler or no filler may be advisable. Suitable fillers include reinforcing materials such as silica aerogel, fumed silica, precipitated silica, glass fibers, titanium dioxide, zirconium silicate, iron oxide, calcium carbonate, diatomaceous earth and carbon black, and extending materials such as ground quartz and polyvinyl chloride, as well as mixtures thereof. It is frequently advantageous to pretreat a silica filler with an activating agent such as octamethylcyclotetrasiloxane.

Various amines and quanidines, optionally alkoxysilyl-substituted, are known to be useful as curing accelerators (component J). Suitable accelerators are disclosed, for example, in the aforementioned U.S. Pat. No. 4,517,337.

The preparation and properties of the compositions of the present invention is illustrated by the following examples. Parts are by weight. All RTV compositions were prepared by conventional high-shear mixing techniques in a nitrogen atmosphere, under the equivalent of "dry box" conditions. Viscosities are Brookfield viscosities at 25° C.

EXAMPLE 1

A mixture of 10 parts (560 mmol.) of 3-aminopropyltrimethoxysilane and 4.92 parts (560 mmol.) of methyl glycidyl ether was heated under reflux in a nitrogen atmosphere. The progress of the reaction was followed by gas chromatography, which showed the reaction to be complete after 1½ hours. Volatile materials were removed in vacuum, yielding the desired composition containing 1,1-dimethoxy-3-methoxymethyl-1-sila-2-oxa-4-azacyclooctane. Its molecular structure was confirmed by gas chromatographic mass spectroscopy.

EXAMPLE 2

An RTV composition was prepared by initially blending 100 parts of a polymethoxysilyl-terminated polydimethylsiloxane having a viscosity of 300 poises, 0.68 part of methyltrimethoxysilane, 16 parts of octamethylcyclotetrasiloxane-treated fumed silica and 23 parts of a trimethylsilyl-terminated polydimethylsiloxane, and subsequently adding 0.42 part of dibutyltin bis(acetylacetonate), 0.28 part of acetylacetone, 0.35 part of methyltrimethoxysilane, 1.0 part of CETMS and 0.7 part of the product of Example 1. Adhesion-in-peel on unprimed aluminum was determined according to ASTM test method C794 after 7 days of cure at 50% relative humidity, and are reported in millipascals.

Comparison was made with the following controls:

Control A—a composition prepared similarly, substituting 0.7 part of acetoxypropyltrimethoxysilane for the product of Example 1.

Control B—a composition prepared by a similar method except that the CETMS was introduced in the first blending step, 1.4 parts of methyltrimethoxysilane was employed and all of it was introduced in the second blending step, and 0.7 part of isocyanatopropyltrimethoxysilane was substituted for the product of Example 1.

Control C—a composition prepared like Control B, substituting 0.7 part of glycidoxypropyltrimethoxysilane for the isocyanatopropyltrimethoxysilane.

The product of Example 1 gave an adhesion value of 165.5 millipascals, while each control gave a value less than 35 millipascals.

What is claimed is:

1. A composition comprising cyclic aminoalkylsilanes having the formula (I)

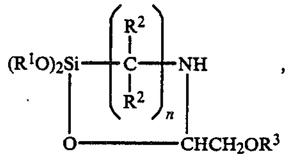

wherein $R^1$ is $C_{1-8}$ alkyl, each $R^2$ is independently hydrogen or $C_{1-4}$ primary or secondary alkyl, $R^3$ is methyl or ethyl and n is 2 or 3.

2. A composition according to claim 1 wherein $R^1$ is methyl and $R^2$ is hydrogen.

3. A composition according to claim 2 wherein $R^3$ is methyl.

4. A composition according to claim 3 wherein n is 3.

* * * * *